United States Patent
Ramachandran et al.

(10) Patent No.: US 9,522,045 B2
(45) Date of Patent: Dec. 20, 2016

(54) DISTORTION FINGERPRINTING FOR EM TRACKING COMPENSATION, DETECTION AND ERROR CORRECTION

(71) Applicant: KONINKLIJKE PHILIPS N.V., Eindhoven (NL)

(72) Inventors: Bharat Ramachandran, Morganville, NJ (US); Ameet Kumar Jain, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 265 days.

(21) Appl. No.: 14/363,671

(22) PCT Filed: Nov. 14, 2012

(86) PCT No.: PCT/IB2012/056404
§ 371 (c)(1),
(2) Date: Jun. 6, 2014

(87) PCT Pub. No.: WO2013/088278
PCT Pub. Date: Jun. 20, 2013

(65) Prior Publication Data
US 2014/0354300 A1    Dec. 4, 2014

Related U.S. Application Data

(60) Provisional application No. 61/569,918, filed on Dec. 13, 2011.

(51) Int. Cl.
*G01R 23/20*    (2006.01)
*G01R 29/26*    (2006.01)
*A61B 19/00*    (2006.01)
*G01R 23/00*    (2006.01)
*A61B 6/00*    (2006.01)
*G01R 29/08*    (2006.01)

(52) U.S. Cl.
CPC .......... *A61B 19/5244* (2013.01); *A61B 6/4441* (2013.01); *A61B 6/547* (2013.01); *A61B 34/20* (2016.02); *G01R 23/00* (2013.01); *G01R 29/0814* (2013.01); *G01R 29/26* (2013.01); *A61B 2034/2051* (2016.02)

(58) Field of Classification Search
CPC ..... G01R 29/0814; G01R 27/28; G01R 29/26; G01R 23/00; G01R 31/001; A61B 6/4441; A61B 6/547; A61B 19/5244
USPC .......................... 324/654, 649, 600, 750.12, 750.03,324/750.01, 537, 500, 144, 76.11, 612, 613,324/620, 628, 207.12
See application file for complete search history.

(56) References Cited

U.S. PATENT DOCUMENTS 6,184,693 B1 * 2/2001 Arai ................... G01R 29/0814
324/144
2005/0107687 A1    5/2005 Anderson
(Continued)

FOREIGN PATENT DOCUMENTS

WO    WO2011110966    9/2011

*Primary Examiner* — Hoai-An D Nguyen

(57) ABSTRACT

A system for accounting for electromagnetic (EM) distortion with an EM tracking system includes a sensor array (144) configured to sense EM energy in a target volume. An EM sensing correction module (140) is configured to analyze data from the sensor array to detect EM distorters in the target volume. The EM sensing correction module is further configured to compare distortion fingerprints stored in a database (142) to identify a distortion source.

22 Claims, 6 Drawing Sheets

(56) References Cited

U.S. PATENT DOCUMENTS

| | | | |
|---|---|---|---|
| 2005/0159109 A1* | 7/2005 | Kivekas | H04B 1/715 |
| | | | 455/67.11 |
| 2008/0200927 A1 | 8/2008 | Hartmann et al. | |
| 2010/0082280 A1 | 4/2010 | Schneider | |
| 2011/0095934 A1* | 4/2011 | Freeman | G01R 29/0892 |
| | | | 342/13 |
| 2015/0012222 A1* | 1/2015 | Warner | A61B 5/04012 |
| | | | 702/19 |

* cited by examiner

US 9,522,045 B2

DISTORTION FINGERPRINTING FOR EM TRACKING COMPENSATION, DETECTION AND ERROR CORRECTION

CROSS-REFERENCE TO PRIOR APPLICATIONS

This application is the U.S. National Phase application under 35 U.S.C. §371 of International Application Serial No. PCT/IB2012/056404, filed on Nov. 14, 2012, which claims the benefit of U.S. Application Ser. No. 61/569,918, filed on Dec. 13, 2011. These applications are hereby incorporated by reference herein.

This disclosure relates to electromagnetic (EM) tracking and more particularly to systems and methods for distortion fingerprinting to improve EM tracking accuracy.

EM tracking employs a field generator that produces spatially-varying magnetic fields which induce currents in sensor coils. A measurement system is then used to calculate the position and orientation based on measured voltages. EM tracking techniques provide real-time position and orientation information in three-dimensional (3D) space and are used to aid interventional procedures. Since the size of these sensor coils is very small, they can be embedded into a catheter or other device and may be used for guided navigation. As a result, EM tracking systems are very well suited for in-body interventions. The presence of ferromagnetic or paramagnetic conductors such as in medical equipment can distort the EM field, and electromagnetic interference from nearby electronics is known to reduce the accuracy of EM tracking. As a result, there is no sure way for the interventionist to know if a point being tracked is accurate.

Metallic surgical tools induce distortions in an electromagnetic (EM) field, which can compromise achievable navigation accuracies during EM tracking. For example, an X-ray detector introduces distortions during procedures in an interventional laboratory. Different approaches to provide quality control include detection and compensation for error caused by large metallic distorters during EM tracking. One such scheme for real-time estimation of error confidences is based on calibration wands. Another focuses on intelligently positioning the patient or the imager. Other techniques rely on calibration phantoms and known sensor geometry or calibrations between EM and other imaging modalities like X-ray or ultrasound images to provide intra-operative quality control.

In accordance with the present principles, a system for accounting for electromagnetic (EM) distortion with an EM tracking system includes a sensor array configured to sense EM energy in a target volume. An EM sensing correction module is configured to analyze data from the sensor array to detect EM distorters in the target volume. The EM sensing correction module is further configured to compare distortion fingerprints stored in a database to identify a distortion source.

A system for accounting for electromagnetic (EM) distortion with an EM tracking system includes a database constructed by storing a plurality of characterized distortion morphologies as fingerprints associated with tools, devices and combinations thereof that cause distortions to an EM field. A sensor array is configured to intra-operatively sense EM energy in a target volume. An EM sensing correction module is configured to analyze data from the sensor array to detect EM distorters in the target volume. The EM sensing correction module is further configured to compare distortion fingerprints stored in the database to identify a distortion source and to output one or more of a position and orientation of a distorter, an error map showing error introduced by a distorter or an identification of an unknown distorter.

A method for accounting for electromagnetic (EM) distortion with an EM tracking system includes measuring EM errors using a sensor array configured to sense EM energy in a target volume; comparing distortion fingerprints stored in a database to identify a distortion source by analyzing data from the sensor array in the target volume; and outputting one or more of a position and orientation of a distorter, an error map showing error introduced by a distorter or an identification of an unknown distorter.

This disclosure will present in detail the following description of preferred embodiments with reference to the following figures wherein.

Figure 4:
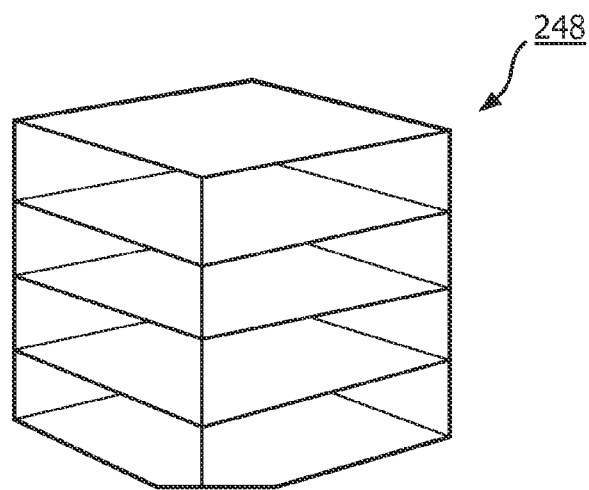
Figure 5:
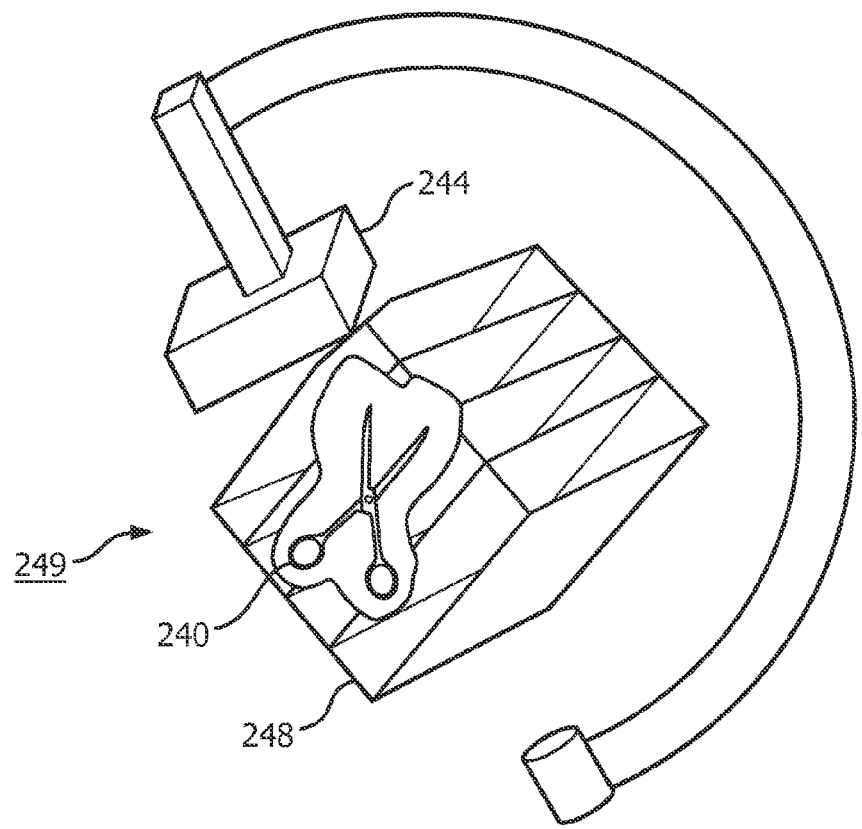
Figure 6:
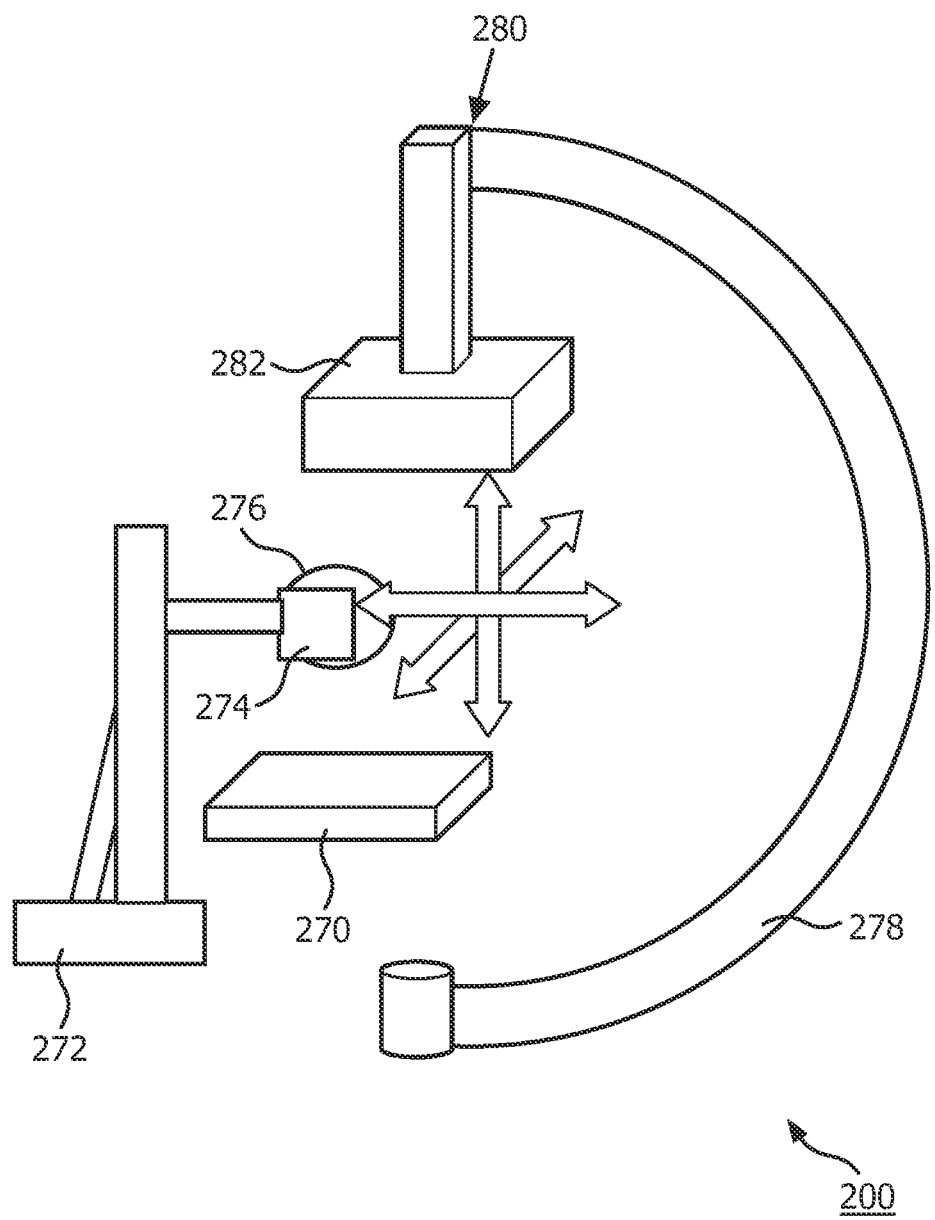
Figure 7:
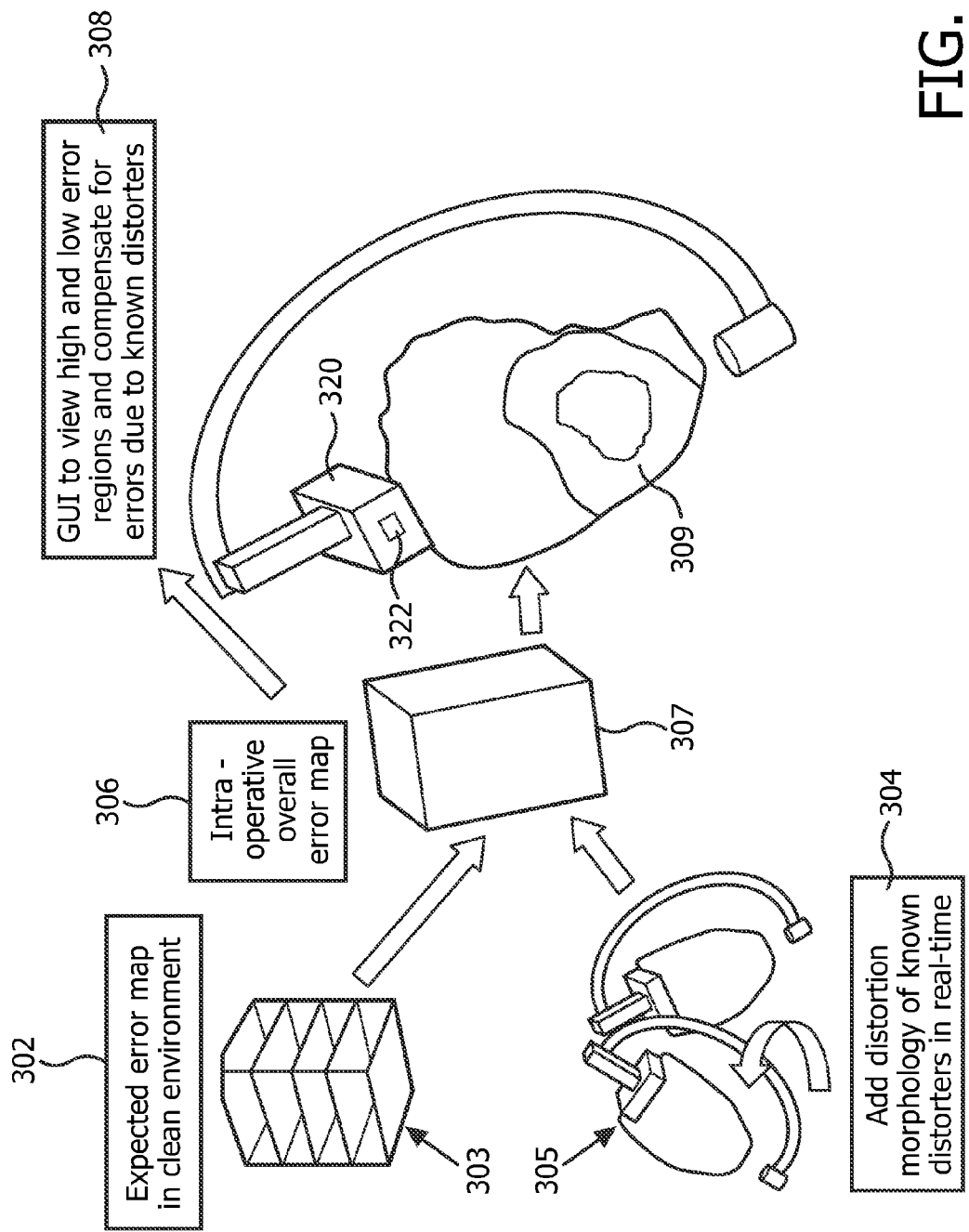
Figure 8:
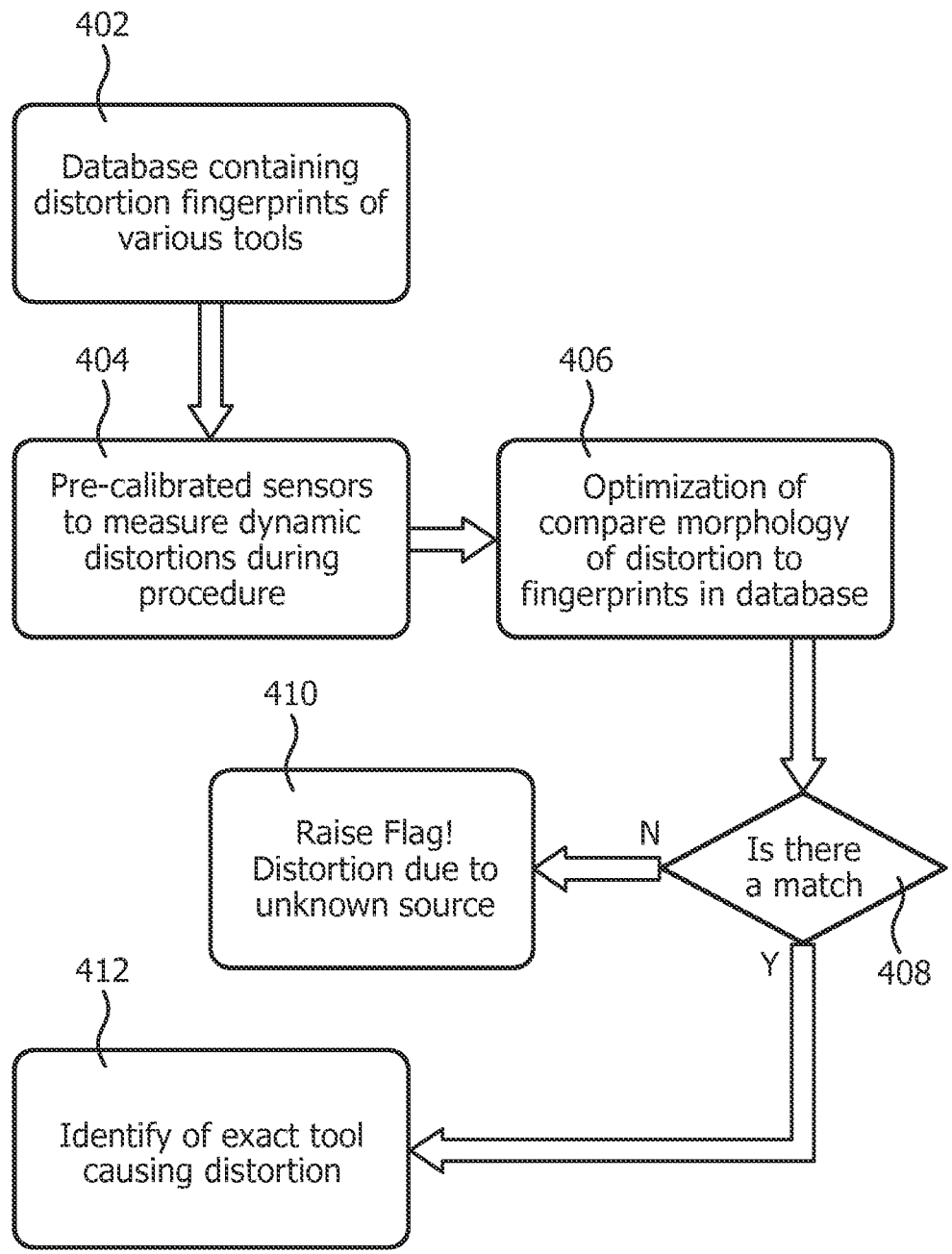

FIG. 4 illustratively shows a spatial representation of an EM field with no distorters (clean environment) in accordance with one illustrative embodiment;

FIG. 5 illustratively shows a spatial representation of an EM field with distortion from a C-arm detector and a scissor to show overall error due to the clean environment background and due to the distorters in accordance with one illustrative embodiment;

FIG. 6 is a schematic diagram showing a robot configured to sense an EM field due to a C-arm detector in a target volume area to characterize the C-arm detector's distortion morphology (fingerprint) in accordance with one illustrative embodiment;

FIG. 7 is a block/flow diagram showing a method for generating error maps for EM distortion compensation in accordance with one illustrative embodiment; and FIG. 8 is a block/flow diagram showing a method for determining an unknown EM distortion source in accordance with one illustrative embodiment.

In accordance with the present principles, EM distortion fingerprints are employed to generate real-time error maps permitting visualization of regions of low and high error within a tracking volume. Furthermore, by knowing the identity of a distorter, its location and error induced, a system can compensate for the errors from expected distorters thus increasing the accuracy during tracking. In one embodiment, distortion fingerprinting is employed to establish error maps and visualize regions of good and poor accuracy within the tracking volume—intra-operatively. The embodiments can also add distortion morphologies of known tools to the overall error map by having sensors mounted on the tools and can compensate for errors that are induced by known distorters.

An error map may be created for an entire region to visualize regions of low and high error intra-operatively. For example, if a distorter is moving in the field, the error map and the regions with good and poor accuracy also change while being viewed during an operation. By knowing the identity and position of the distorter and its fingerprint, the contribution of its distortion to overall error can be computed and thus, errors caused by known distorters can be compensated.

In another embodiment, the distorters (like a detector or a surgical probe) are intra-operatively identified using the distortion fingerprints. By comparing the fingerprints to a database and running an optimization scheme, an exact tool or combination of tools can be identified that are causing the distortion. The system can, in conjunction with pre-calibrated sensors that dynamically measure errors, also be employed to detect the presence of unknown distorters and raise a flag if an unknown source is discovered. The ability of a tool to produce distortions in an EM field varies and depends on its size, shape and the material it is composed of. Each distorter has a unique distortion morphology, for example, the distortion patterns from a C-arm detector are known to be very different from those of an ablation catheter. A database is created and stores distortion fingerprints of various known objects. A sparse set of pre-calibrated EM sensors are employed to compute the expected distortion in a 'clean' environment versus dynamic distortion induced on the sensors during a procedure. An optimization scheme is employed to identify the presence of one or more distorters within the EM field by computing error contributions at measurement points. The amount of error can be differentiated between expected distorters and the overall distortion to identify if a known distorter is present in the field. A flag or warning is raised if distortions are detected due to unknown distorters.

In yet another embodiment, distortion fingerprinting is employed to characterize distortion morphology of known objects. After an initial calibration, the present system can, in conjunction with pre-calibrated sensors that dynamically measure errors, be employed to identify and localize the distorter. All distorters have a unique morphology and a varying reach to which the distorter distorts (due to varying morphology). This variable reach and variable distorting morphology may be leveraged to intra-operatively detect the location of the distorting element. A sparse set of pre-calibrated EM sensors, the expected distortion in a 'clean' environment and dynamic distortion induced on the sensors during the procedure may be employed to compute error contribution. Pre-computed morphology of the distorter (e.g., a detector) has its error 'contribution' computed at the measurement points. If the contribution is beyond an acceptable threshold, a warning may be raised. The amount of error can be differentiated from 'expected' distorters from that of the overall distortion.

It should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Figure 1:
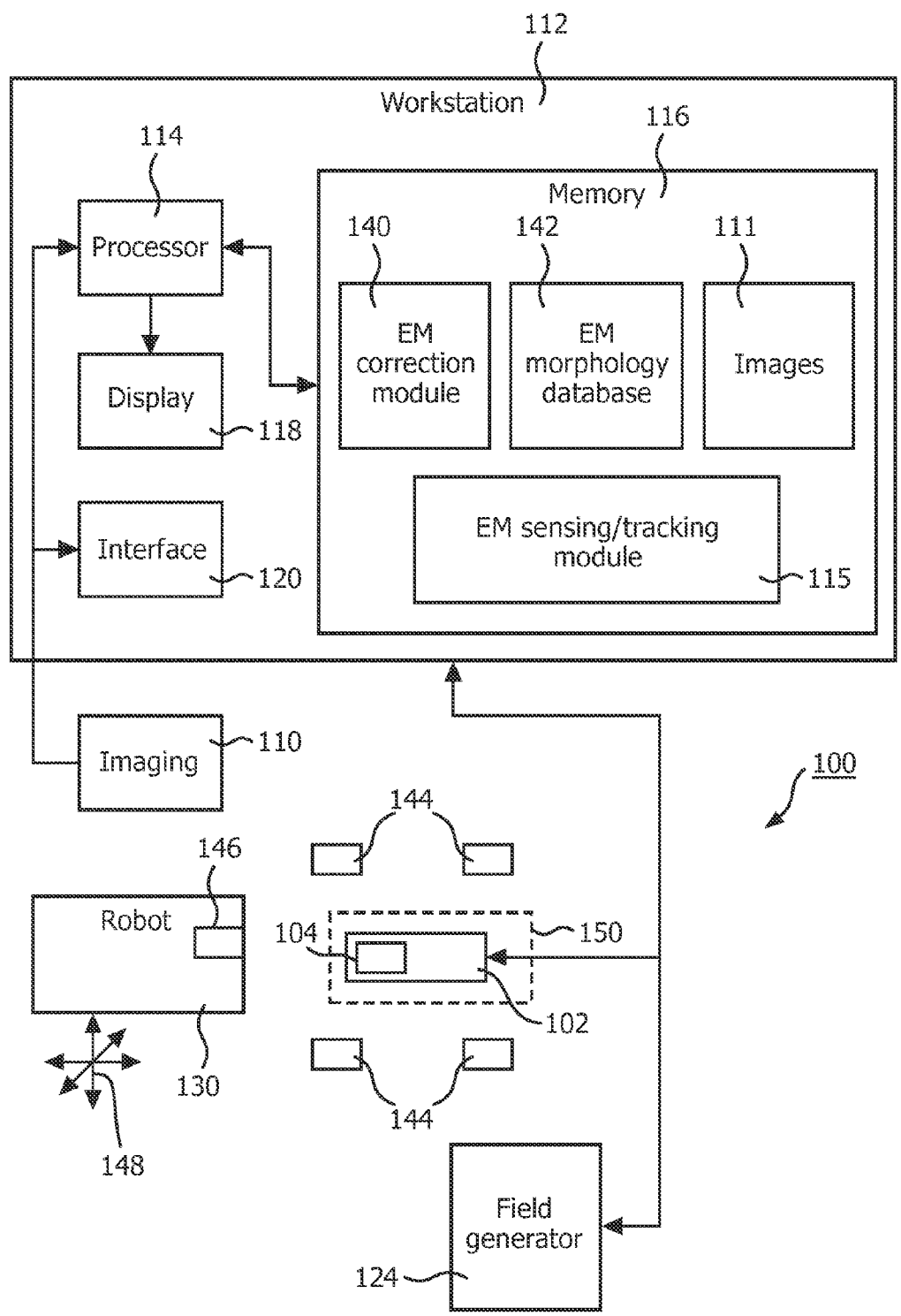
FIG. 1 is a block/flow diagram showing a system for accounting for EM error due to distorters in an EM tracking environment in accordance with one illustrative embodiment.

Referring now to the drawings in which like numerals represent the same or similar elements and initially to FIG. 1, a system 100 for performing a medical procedure is illustratively depicted. System 100 may include a workstation or console 112 from which a procedure is supervised and managed. Workstation 112 may also include an apparatus for collecting EM morphologies for characterizing EM distorters. Workstation 112 preferably includes one or more processors 114 and memory 116 for storing programs and applications. Memory 116 may store an EM sensing module 115 configured to interpret feedback signals from an EM sensing/tracking device 104. In one embodiment, sensing module 115 is configured to use EM signal feedback from EM sensing devices 104 to reconstruct EM space and track medical instruments or devices 102. A medical device or tool 102 may include an instrument having an EM tracking sensor 104 mounted thereon or therein. Device 102 may include, e.g., a catheter, a guide wire, an endoscope, a probe, a robot, an electrode, a filter device, a balloon device, or other medical component, etc. Workstation 112 may include a display 118 for viewing internal images of a subject if an imaging system 110 is employed. The imaging system 110 may include, e.g., a magnetic resonance imaging (MRI) system, a fluoroscopy system, a computed tomography (CT) system, ultrasound (US), etc. Display 118 may also permit a user to interact with the workstation 112 and its components and functions. This is further facilitated by an interface 120 which may include a keyboard, mouse, a joystick or any other peripheral or control to permit user interaction with the workstation 112. Display 118 may also permit a user to view error maps, warning alerts, distortion fingerprints, etc.

A field generator 124 is preferably installed in a vicinity of a patient or a target volume 150 so that the generator and the EM sensor or sensors 104 occupy a same environment. Sensing device 104 preferably includes one or more coils which are employed to detect of changes in EM field due to their movement. In this way, the coils of the sensors 104 permit tracking of instrument or device 102 relative to the patient and/or the tracking volume 150.

As described above, metallic objects and electronic equipment can produce distortions in local magnetic fields and influence readings of the EM sensors 104. The present principles provide an EM sensing correction module 140 that may include one or more features for reducing distortions in the environment surrounding the tracking volume 150. The module 140 is configured to characterize distortions, e.g., as a measurement of a signature or fingerprint of the field distortion created by tools or objects in or near the target volume 150. The characterization of these fingerprints is performed in advance of any procedure and the fingerprints or distortion morphologies are stored in a database 142 where the fingerprints measured in real-time are correlated with identities of the objects that created the fingerprints. The module 140 is configured to provide one or more of the following task identify distorters (objects), optimize or filter the distortions present to more accurately track or sense EM radiation, sense a change to the EM field, warn of EM field changes, etc. These functions will be described in greater detail herein. The module 140 may consult and store information in the database 142 which may include a portion of memory 116. The database 142 may store the signatures of distortion elements in the environment or may store signatures for general tools and/or instruments employed in the environment.

System 100 may undergo training where the module 140 is employed to characterize distortion morphology (or reach) of any known object. Each object is characterized to measure its signature or fingerprint so that it may be identified in more general EM fields. This may be done in isolation or separately from using the system 100 for more accurately EM tracking a device during a procedure. In one example, a robot 130 is employed with an EM sensor(s) 146 to characterize the space. The robot 130 may be moved about the target volume 150 or environment as indicted by coordinates 148 to measure EM fields in the region. The robot 130 may be employed to characterize the background EM fields (clean environment) as a baseline reference and also characterize the fields about the objects deployed during a procedure. The data collected by the robot 130 can be employed for characterizing tools for the distortion morphologies stored in the database 142. During a procedure, the robot 130 may be employed to measure dynamic changes in the EM field. The robot 130 may not be needed during the procedure as the initial characterization would be completed in advance.

Within the environment, pre-calibrated sensors 144 may also be employed to dynamically measure errors. These sensors 144 are arranged in an array or grid and may be employed in the characterization process with or without the robot 130 and/or during a procedure to provide EM measurements for distorters with or without the robot 130. A distorter's contribution may be measured by the sensors 144 to determine their contribution in the overall error. An approximate location of the distorter can also be estimated intra-operatively from this error contribution.

In another embodiment, the sensors 144 may be employed to generate error maps using the module 140. The error maps may be provided for an entire tracking volume using distortion fingerprinting techniques that provide the identity and location of known distorters in the environment. The error maps provide intra-operative views of regions with low and high error. The maps may be updated for changing errors in real-time to indicate, e.g., the error visualization as a tool moves in the tracking volume. Dynamic changes in the error morphology of a tool or other distortion creating instrument may be tracked for the entire error map by having a tracking device like an EM sensor on the tool to track its location. The errors detected and mapped can be error compensated for known distorters.

In another embodiment, the database 142 stores the fingerprints that characterize the distortion morphology of any known object or device. The pre-calibrated sensors 144 compare expected distortions in a clean environment (reference) to dynamically measured errors during a procedure. The distorter or combination of distorters and their contribution are identified in the overall error. The presence of any unknown distorters is detected. In the event that a new distortion is detected, a warning may be indicated on the display 118 or at the interface 120.

Imaging system 110 may optionally be provided for collecting pre-operative imaging data or real-time intra-operative imaging data. The pre-operative imaging may be performed at another facility, location, etc. in advance of any procedure. Images 111 may be stored in memory 116, and may include pre-operative 3D image volumes of the target volume 150 as needed.

Figure 2:
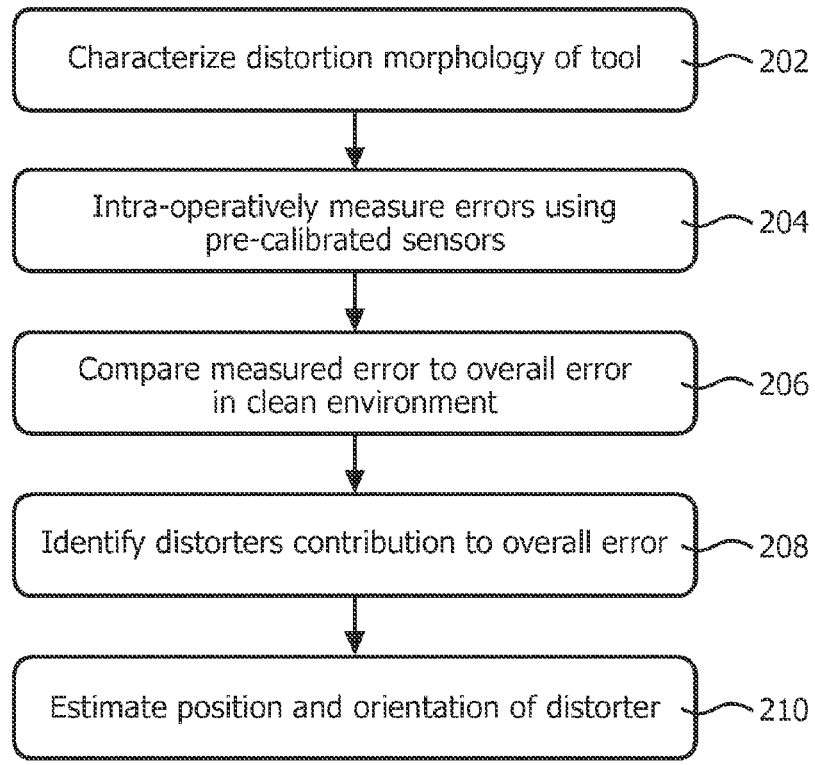
FIG. 2 is a block/flow diagram showing a method for identifying distorters, their position and orientation in accordance with one illustrative embodiment.
Figure 3:
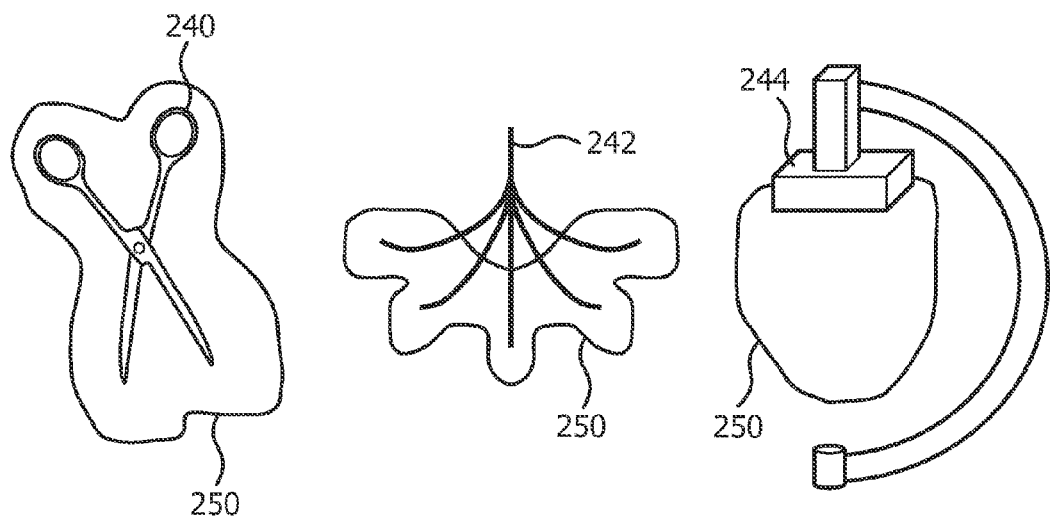
FIG. 3 is a diagram illustratively showing distortion created by three examples of distortion sources (e.g., a scissor, an ablation probe and a detector of a C-arm)

Referring to FIG. 2 with continued reference to FIG. 1, a block/flow diagram for characterizing distorters such as tools, instruments or devices to create a fingerprint or EM signature associated with the distorters is illustratively shown. The fingerprint is preferably employed for estimating the distorter's location and orientation. In block 202, a distortion morphology (or reach) of any known object is characterized (fingerprint). EM signatures are generated using the EM generator 124 to create a field that is distorted by the object. FIG. 3 illustratively shows examples of field distortions 250 due to a scissors 240, an ablation probe 242 and a C-arm detector 244 for an X-ray machine. In block 204, errors in EM fields are measured intra-operatively using the sensors 144 (and/or robot 130). FIG. 4 illustratively shows an error map 248 for EM space in a "clean" environment. The clean environment represents a baseline reference EM field without distorters. In block 206, the measured error in the clean environment is compared to overall error (error combined from all sources) with one or more distorters in block 206. Error measured during a procedure (live with all the distortions, e.g., arising from a detector, table, tool, etc.) is compared with what was measured in the "clean environment" (no distortions). The variation between these two error maps permits finding what portion of the overall error is caused due to a distorter.

Each distorter's contribution may be identified in the overall error in block 208. An approximate location and orientation of the distorter can also be estimated from this error contribution in block 210. FIG. 5 shows scissors 240 in an EM environment in the vicinity of a C-arm detector 244. The scissors' signature and the detector's signature can be identified in an overall EM field signature 249 by subtracting out the reference baseline (248) from the measured error and comparing the remaining signature to the distortion morphologies stored in the database (142).

In this way, metallic distorters (like a surgical tool) or electronic devices which cause error in a EM tracking can be identified within the EM field. If the type of distortion is known, the system can localize the position and orientation of the tool causing the distortion. This can account for the distorter and make EM tracking measurements more accurate or identify and eliminate the distorter from the environment altogether.

Referring to FIG. 6, another system 200 for characterizing objects is shown in accordance with one illustrative embodiment. It is assumed that a workstation 112 as set forth in FIG. 1 may be employed. However, a separate setup (system 200) for characterization of EM distortion morphologies may be employed. As described in FIG. 1, an EM tracking system including console, sensors and field generator are included and a console unit (e.g., a computer) for performing real-time data processing is also employed. A 3D EM sensor grid 270 is preferably employed for recording the distortion fingerprints of various tools. This sensor grid 270 may be provided at a fixed location around a region or target volume where the EM tracking is employed or the sensor grid 270 may be attached to a robot or other mechanism 272 and moved as needed.

Robot 272 may be fitted with EM sensors 274. The robot 272 is capable of traversing a 3D space for recording the distortion fingerprints of various tools. Metallic surgical tools or electronic devices 276 similar to what might be found in an interventional lab may be connected or placed in a target region near the robot 272. The robot 272 is moved in any direction to collect EM signature (fingerprint) data for the environment (clean) and/or the environment with the distorter (e.g., a detector 282) in it. An X-ray unit 280, specifically with a C-arm 278 is provided in this example for recording its distortion fingerprint, when the C-arm 278 is at different poses and at different source-to-image distances (SIDs).

In one embodiment, a set of EM sensors arranged in 3D space within the EM field in the form of the grid 270 could be used to make field measurements. This may be instead or in addition to using the robot 272. A tool 276 or variety of metallic tools made of different materials that distort the EM field could be brought near this sensor arrangement or grid 270, positioned in different orientations and at different distances from the sensor grid 270, and the distortion fingerprints due to the tool 276 could be learned and stored in the database (142, FIG. 1). For example, in one instance, the detector 282 of the C-arm 278 could be the tool causing distortion and may be placed in a known position (known SID, and orientation say, anterioposterior (AP)) and the sensor arrangement 270 could be positioned on a patient table. Assuming the position of the field generator (124, FIG. 1) and height of the patient table remains the same, the distortion fingerprint due to the detector 282 of the C-arm 278 at a given distance and orientation could be stored and learned by the system 200. In another example, the tool 276 may be attached to the robot 272 or other device and characterized by moving in the field sensed by the grid 270.

In another embodiment, instead of using an EM sensor grid arrangement in 3D space that would require a large number of EM sensors, one or more EM sensors 276 could be mounted on the robot 272 for tracking position. The robot 272 could traverse the 3D space within the EM field and if the distorter (say the detector 282 of the C-arm 278) is placed around the volume traversed by the robot 272, the distortion fingerprint could be learned and stored over time.

In addition to or instead of mounting one or more sensors on the robot 272, other tracking devices may be employed, which include one or more of optical tracking using passive markers, optical tracking using active light emitting diodes (LED), markers using optical shape sensing based on fiber Bragg gratings (FBG) or a plurality of FBGs, optical shape sensing based on refraction and/or scatter or backscatter patterns, markers which may be visible in imaging modalities like an Iodine-based marker which is visible in X-ray or fluoroscopic imaging, radioactive or radio-opaque markers visible in nuclear imaging techniques like positron emission tomography (PET) and/or single photon emission computed tomography (SPECT), markers visible in magnetic resonance imaging (MRI), ultrasound or high frequency ultrasound, computed tomography (CT) or other imaging modalities.

In a clinical setting, if EM tracking is being used for guided navigation, the system 200 could be used to perform comparisons of the distortions at the limited EM sensor positions with the pre-operative morphologies or patterns saved to the database (142, FIG. 1) to identify the tool that is causing the distortion. For example, during an electro-physiology procedure performed in the interventional lab, the EM sensor readings could be used by the system 200 to identify the distortions that are induced by the detector 282 of the C-arm 278 being in close proximity to the patient.

The system could be used to identify the distorter's contribution to the overall error by performing comparisons with pre-operative patterns saved in the database (142). For example, if the pose of the C-arm 278 and the distance of the detector are known, the technique could identify the error caused due to the detector 282 and compare that to the overall error. In a clinical setting, if the source of the distortion is known, the system could be employed to localize the source of this distortion. In other words, if the tool inducing distortions is the detector 282 of the C-arm 278, then the position and orientation of the detector 282 and C-arm 272 could be predicted based on comparisons with the saved distortion fingerprints.

Distortion fingerprinting can be employed to detect, identify and locate a distorting tool within a tracking volume. The methods may be employed to establish expected error maps for the entire volume using the expected error information from a clean environment and pre-calibrated sensors which have identified and located distorters, thus adding their distortion morphologies to the overall error map.

Referring to FIG. 7, a method for developing error maps is illustratively shown. In block 302, an expected error map 303 is generated in a clean environment without distorters. In block 304, error maps 305 are established for an entire tracking volume using distortion fingerprinting techniques that provide the identity and location of known distorters. The distortion morphologies are added to the clean map 303 to produce an overall map 307 in real-time, in block 306. An intra-operatively visualized error map is generated with regions of different (low and high) error. This provides the overall error map 307, which combines sensor data from the error map of the clean environment and the distortion morphology of the distorters. The error visualization is updated in real-time as a tool (e.g., detector 320) moves in the tracking volume thus changing errors. In this way, the error morphology of a tool can be added dynamically to the entire error map by having a tracking device like an EM sensor on the tool (e.g., detector 320) thus tracking its location. In block 308, a graphical user interface (GUI) on a display may be provided to view the high and low error regions on an error map 309. The system 100 compensates for errors induced due to known distorters, e.g., in EM tracking sensing data.

Regions of low and high error are visualized using the overall error maps. For example, a clinician might want to see regions with error less that 2 mm. The module 140 (FIG. 1) would mark out regions corresponding to low error (less than 2 mm) and display them to the clinician on the display 118. The system 100 can compute and visualize the error maps in a real-time manner, thus making the maps available for use intra-operatively when a distorter like a surgical tool is being operated and moved dynamically in a volume of interest. In an additional embodiment, a tracking sensor 322, e.g., an EM sensor or other sensor may be placed on a known tool and its location can be determined in real-time. Thus, stored distortion morphology of that tool could be dynamically added to the overall error map and be visualized by the clinician intra-operatively. In addition, by knowing the errors that are induced in the tracking volume due to known distorters, the generation or error maps can be employed to compensate for these known errors, thus increasing the accuracy as well as the confidence of a clinician while performing a procedure.

Referring to FIG. 8, the system 100 can perform other tasks or functions in addition to those already described. In accordance with one embodiment, a method is provided for warning of unknown distorters in an EM field. In block 402, a database is constructed as described above for storing fingerprints that characterize the distortion morphology of any known object or potentially employed object during a procedure. Input from a database (142, FIG. 1) may include various stored distortion fingerprints that characterize the distortion morphology of known tools. This distortion fingerprinting would be performed by the method described above and depicted in illustrative examples of FIG. 3. In block 404, pre-calibrated sensors are employed to compare expected distortions in a clean environment to dynamically measured errors during a procedure. The pre-calibrated sensors (144, FIG. 1) may include a grid of sensors to compare the expected distortions in a clean environment versus the dynamically measured errors during a procedure.

In block 406, the distorter or combination of distorters are analyzed and/or optimized so that their fingerprints can be compared to the database to identify their contribution in the overall error that is measured. An optimization algorithm/objective function may be employed intra-operatively to perform comparisons of the pre-operative stored distortion maps with measured results. The optimization seeks to find a best match of the morphology of distortions to the database and determine if distortion is due to known or unknown distorters. The comparisons as described here may employ pixel map renditions of the error maps, distortion fields, etc. The pixel values of the images or renderings may be employed for comparisons. Such comparison techniques may employ known methods for comparing images or the like.

In block 408, if there is a match of the measured distortion to a stored distortion fingerprint, then the identity of the distorter is returned in block 412. Otherwise, if the distortion is due to an unknown source, a warning (raise flag) is given. Detection of distortions being caused by some unknown source would show a high error rate during EM tracking. It should be understood that the system 100 may be adjusted to detect any change in the distortion pattern and raise a flag for any change to the distortion pattern (error map).

These features/methods performed by system 100 can intra-operatively identify the exact tool or combination of tools that are causing distortion in the EM field. The system 100 can also detect the presence of unknown distorters during EM tracking and provide a warning. As output, the exact tool or combinations of tools in the EM field which is/are causing the distortion can be identified.

The systems and methods described herein may be employed in procedures for minimally invasive surgery that employ EM tracking techniques, especially in the domain of image guided interventions and therapy. However, the present principles may be applied to other areas in the medical field and in other fields where EM tracking may be employed.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function; and
 e) no specific sequence of acts is intended to be required unless specifically indicated.

Having described preferred embodiments for distortion fingerprinting for EM tracking compensation, detection and error correction (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for accounting for electromagnetic (EM) distortion with an EM tracking system, comprising:
 a sensor array configured to sense EM energy in a target volume; and
 an EM sensing correction module configured to analyze data from the sensor array to detect and identify EM distorters including untracked EM distorters in the target volume, the EM sensing correction module further configured to compare distortion fingerprints stored in a database that are correlated with identities of known objects to identify a distortion source.

2. The system as recited in claim 1, further comprising a robot configured to move in a region associated with the target volume to measure or determine changes to an EM field.

3. The system as recited in claim 2, wherein the robot includes a tracking device to determine its position and orientation.

4. The system as recited in claim 1, wherein the database is constructed by characterizing a plurality of distortion morphologies associated with tools, devices and combinations thereof.

5. The system as recited in claim 1, wherein the sensor array intra-operatively measures EM error and the EM sensing correction module generates error maps.

6. The system as recited in claim 1, wherein the EM sensing correction module estimates error contribution by distorters and identifies the distorter and its position based by comparing measured error with a baseline reference.

7. The system as recited in claim 1, wherein the EM sensing correction module identifies an unknown source of distortion by comparing a distortion source to known distortion morphologies in the database.

8. The system as recited in claim 1, wherein the EM sensing correction module estimates an error contribution by distorters and compensates for the error to improve EM tracking accuracy.

9. A system for accounting for electromagnetic (EM) distortion with an EM tracking system, comprising:
 a database constructed by storing a plurality of characterized distortion morphologies associated with tools, devices and combinations thereof that cause distortions to an EM field wherein said characterized distortion morphologies represent distortion fingerprints associated with the tools, devices and combinations thereof;
 a sensor array configured to intra-operatively sense EM energy in a target volume; and
 an EM sensing correction module configured to analyze data from the sensor array to detect and identify EM distorters including untracked EM distorters in the target volume, the EM sensing correction module further configured to compare distortion fingerprints stored in the database that are correlated with identities of known objects to identify a distortion source, the EM sensing correction module configured to output one or more of a position and orientation of a distorter, an error map showing error introduced by a distorter or an identification of an unknown distorter.

10. The system as recited in claim 9, further comprising a robot configured to move in a region associated with the target volume to measure or determine changes to an EM field.

11. The system as recited in claim 10, wherein the robot includes a tracking device to determine its position and orientation.

12. The system as recited in claim 9, wherein the sensor array intra-operatively measures EM error and the EM sensing correction module generates error maps.

13. The system as recited in claim 9, wherein the EM sensing correction module estimates an error contribution by distorters and identifies the distorter and its position based by comparing measured error with a baseline reference.

14. The system as recited in claim 9, wherein the EM sensing correction module identifies an unknown source of distortion by comparing a distortion source to known distortion morphologies in the database.

15. The system as recited in claim 9, wherein the EM sensing correction module estimates an error contribution by distorters and compensates for the error to improve EM tracking accuracy.

16. A method for accounting for electromagnetic (EM) distortion with an EM tracking system, comprising:
 measuring EM errors using a sensor array configured to sense EM energy in a target volume;
 comparing distortion fingerprints stored in a database that are correlated with identities of known objects to identify a distortion source including untracked EM distorters by analyzing data from the sensor array in the target volume; and
 outputting one or more of a position and orientation of a distorter, an error map showing error introduced by a distorter or an identification of an unknown distorter.

17. The method as recited in claim 16, further comprising measuring changes to an EM field due to a distorter configured to move in a region associated with the target volume.

18. The method as recited in claim 16, further comprising constructing the database by characterizing a plurality of distortion morphologies associated with tools, devices and combinations thereof.

19. The method as recited in claim 16, wherein outputting includes generating an error map intra-operatively to identify regions of low and high error measurements in the target volume.

20. The method as recited in claim 16, wherein outputting includes estimating an error contribution by distorters and identifying the distorter and its position based by comparing measured error with a baseline reference.

21. The method as recited in claim 16, wherein outputting includes identifying an unknown source of distortion by comparing a distortion source to known distortion morphologies in the database.

22. The method as recited in claim 16, wherein outputting includes estimating an error contribution by distorters and compensating for the error to improve EM tracking accuracy.

* * * * *